US010335270B2

(12) United States Patent
Essinger et al.

(10) Patent No.: US 10,335,270 B2
(45) Date of Patent: Jul. 2, 2019

(54) METHOD AND APPARATUS FOR COMPRESSING/LOADING STENT-VALVES

(75) Inventors: Jacques Essinger, St-Prex (CH); Stephane Delaloye, Bulach (CH); Jean-Luc Hefti, Cheseaux-Noreaz (CH); Luc Mantanus, Lausanne (CH); Michael Paris, Prilly (CH)

(73) Assignee: SYMETIS SA, Ecublens (CH)

( * ) Notice: Subject to any disclaimer, the term of this patent is extended or adjusted under 35 U.S.C. 154(b) by 1322 days.

(21) Appl. No.: 14/115,561

(22) PCT Filed: May 3, 2012

(86) PCT No.: PCT/EP2012/058085
§ 371 (c)(1),
(2), (4) Date: Jul. 1, 2015

(87) PCT Pub. No.: WO2012/150290
PCT Pub. Date: Nov. 8, 2012

(65) Prior Publication Data
US 2015/0297381 A1     Oct. 22, 2015

(30) Foreign Application Priority Data
May 5, 2011 (EP) ...................... 1164926

(51) Int. Cl.
*H02G 1/00* (2006.01)
*A61F 2/24* (2006.01)
*A61F 2/95* (2013.01)
(52) U.S. Cl.
CPC .... *A61F 2/2412* (2013.01); *A61F 2002/9522* (2013.01)

(58) Field of Classification Search
CPC .. A61F 2/95; A61F 2/966; H02G 1/00; H02G 3/00; H02G 16/00
See application file for complete search history.

(56) References Cited

U.S. PATENT DOCUMENTS 5,611,587 A  *  3/1997  Brown ...................... B66C 3/04
                                                            294/106
5,626,604 A      5/1997  Cottone, Jr.
(Continued)

FOREIGN PATENT DOCUMENTS

EP      0916318 A1    5/1999
JP   2002-510526 A    4/2002
(Continued)

OTHER PUBLICATIONS

International Search Report for International Application No. PCT/EP2012/058085, dated Jul. 18, 2012.

*Primary Examiner* — Lee D Wilson
(74) *Attorney, Agent, or Firm* — Seager, Tufte & Wickhem LLP

(57) ABSTRACT

Apparatus (40) for compressing a transcatheter cardiac stent-valve (10) comprises: a hollow channel (42) having an interior surface (50) shaped for progressively compressing the stent-valve in response to longitudinal advancement of the stent-valve within the channel; a driver (46) threadedly engaged on the exterior of the channel for generating a longitudinal driving force in response to rotation; a mover (44) having limbs (56) that project through slots (58) in the channel wall to transmit the driving force to the stent-valve within the channel; and a channel extension (48) removably attachable at the exit (54) to provide a generally cylindrical containment bore (66).

20 Claims, 10 Drawing Sheets

(56) References Cited

U.S. PATENT DOCUMENTS

| | | | | |
|---|---|---|---|---|
| 5,672,169 A | * | 9/1997 | Verbeek | A61F 2/86 606/1 |
| 6,618,921 B1 | * | 9/2003 | Thornton | A61F 2/958 29/235 |
| 9,021,674 B2 | * | 5/2015 | Hillukka | A61F 2/0095 254/134.3 FT |
| 9,308,346 B2 | * | 4/2016 | Soundararajan | A61F 2/95 |
| 2003/0135970 A1 | * | 7/2003 | Thornton | A61F 2/958 29/270 |
| 2007/0061008 A1 | | 3/2007 | Salahieh et al. | |
| 2009/0054976 A1 | | 2/2009 | Tuval et al. | |
| 2009/0299451 A1 | | 12/2009 | Ellsworth et al. | |
| 2012/0103840 A1 | | 5/2012 | McCaffrey | |
| 2012/0158128 A1 | | 6/2012 | Gautam | |
| 2012/0226341 A1 | * | 9/2012 | Schreck | A61F 2/966 623/1.12 |
| 2015/0297381 A1 | * | 10/2015 | Essinger | A61F 2/2412 623/1.12 |

FOREIGN PATENT DOCUMENTS

| | | |
|---|---|---|
| JP | 2005-506873 A | 3/2005 |
| WO | WO-9953864 A1 | 10/1999 |
| WO | WO-2010014834 A1 | 2/2010 |
| WO | 2012155130 A1 | 11/2012 |

* cited by examiner

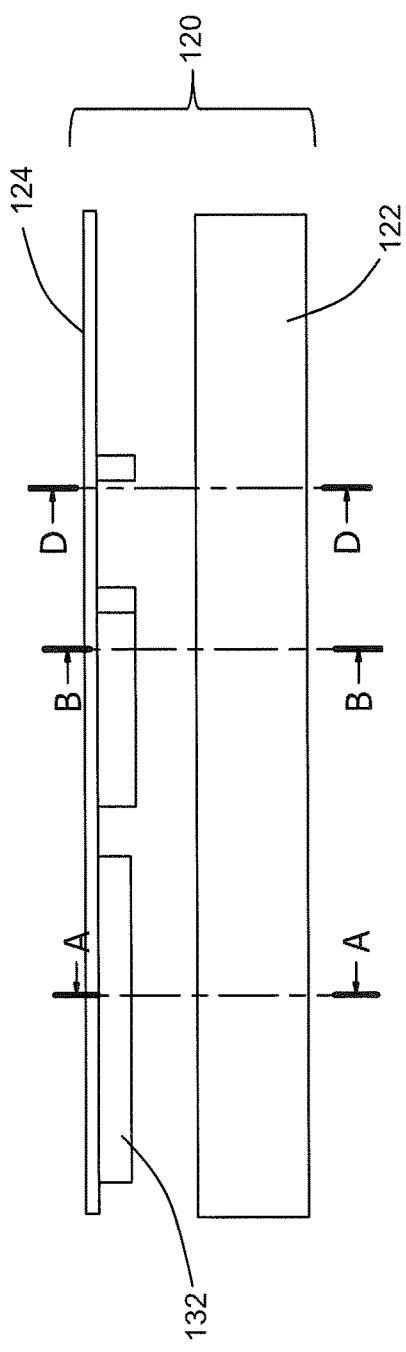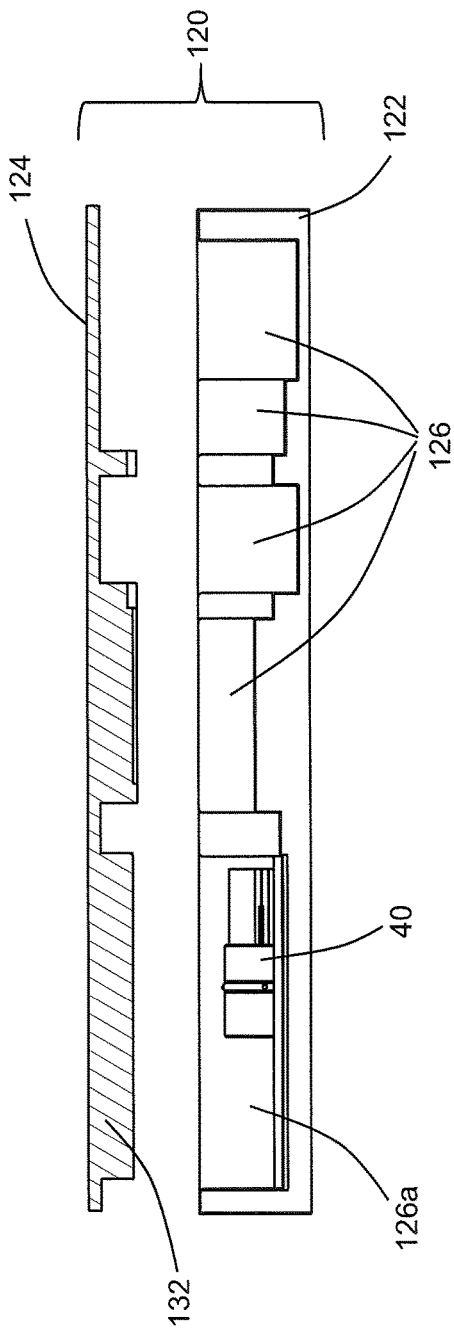
FIG. 8
FIG. 9

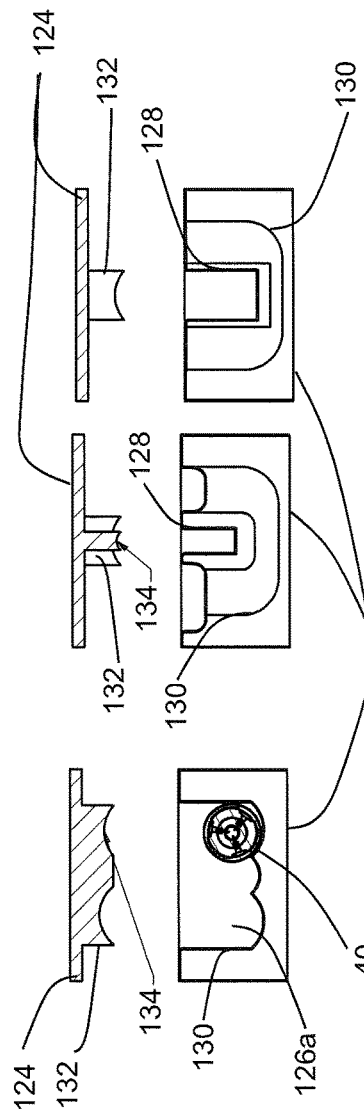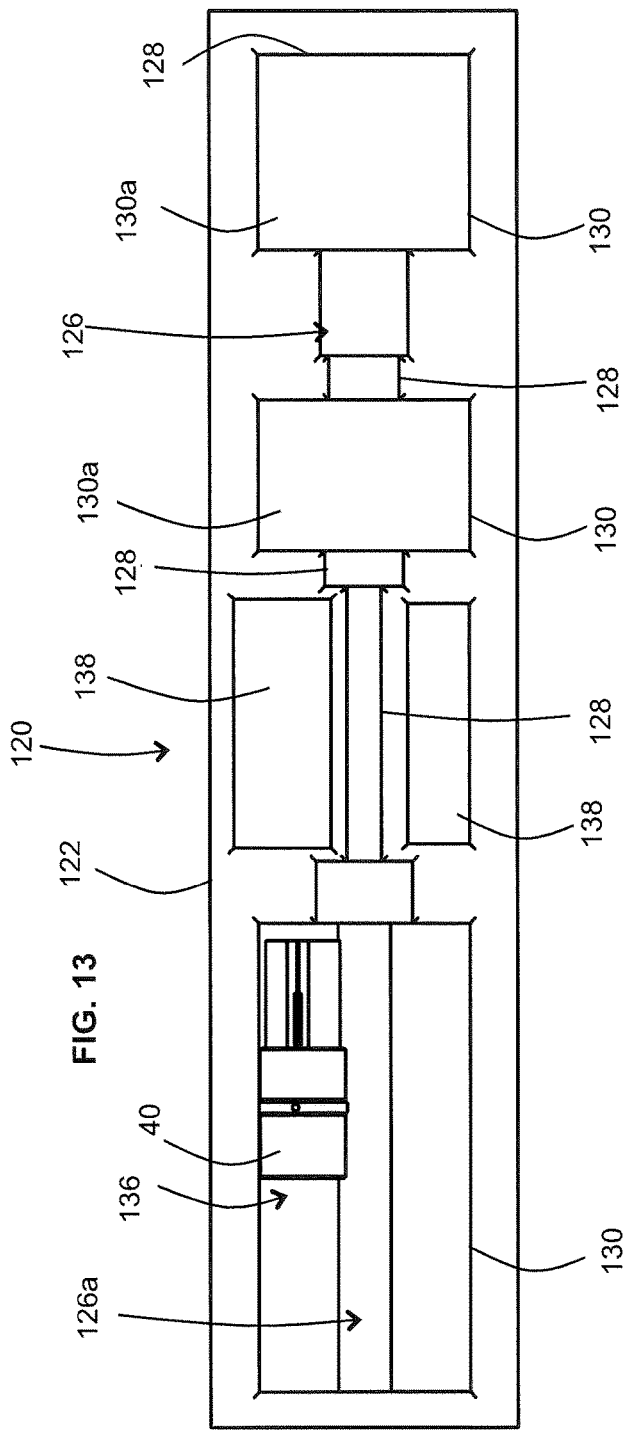

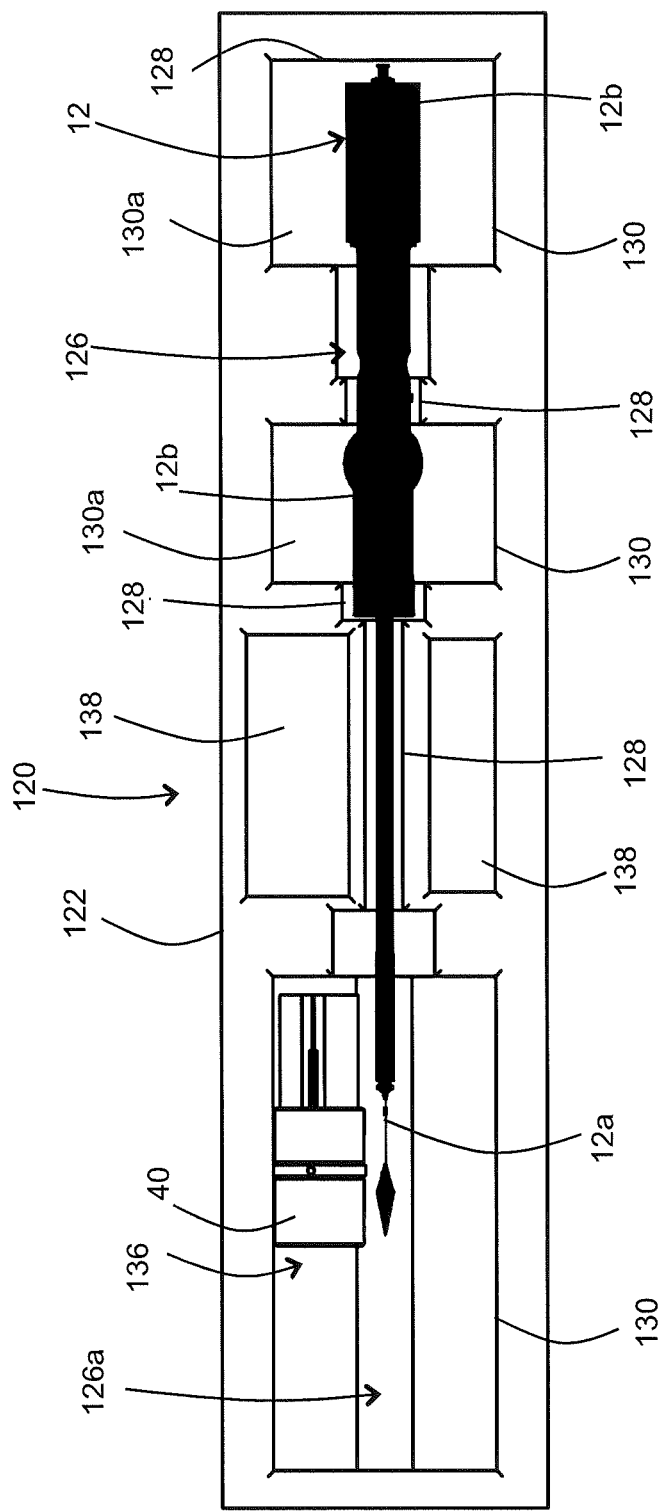

METHOD AND APPARATUS FOR COMPRESSING/LOADING STENT-VALVES

CROSS REFERENCE TO RELATED APPLICATIONS

The present application is a 35 U.S.C. § 371 national stage entry of PCT/EP2012/058085, which has an international filing date of May 3, 2012, and claims priority to European Patent Application No. 11164926.5, filed on May 5, 2011. The present application incorporates herein by reference the disclosures of each of the above-referenced applications in their entireties.

The present invention relates to the field of stents for transcatheter delivery, and in particular to a method and apparatus for compressing a stent to a compressed condition and/or for loading a stent for a delivery catheter. In some non-limiting aspects, the stent is a stent-valve, for example a cardiac stent-valve. The invention has been devised while addressing problems encountered with stent-valves, but the invention may also be applicable for compressing other types of stents for transcatheter delivery.

WO-A-2009/053497 describes cardiac stent-valves and associated methods and systems for delivering the stent-valve via minimally invasive surgery. The stent-valves are compressible to a compressed state suitable to be accommodated at the delivery tip of the delivery catheter. In the compressed state, the small size enables the catheter carrying the stent-valve to be introduced via minimally invasive surgery. Upon release at the desired site of implantation, the stent-valve expands to an operative size.

Further examples of stent-valves, delivery catheters, and/or techniques for compressing the stent-valves for delivery, are described in: US-2009/0171432, WO 2008/035337 and WO 2009/116041.

The task of compressing the stent-valve on to (or ready for) the delivery catheter is complicated because the stent-valve is delicate and vulnerable to damage. Damage may result from over compression, or a non-uniform stress distribution, or buckling, or non-circularity during compression, or from tearing or abrasion of valve component tissue. A deformed or damaged stent-valve may function imperfectly, or have a reduced operational life, or may be difficult or even impossible to implant correctly. The complications are exacerbated in the case of a self-expanding type of stent-valve because a self-expanding stent-valve has a strong restoration force when compressed, and requires application of a large compression force to compress the stent-valve down to its compressed condition. Large forces are difficult to apply to a delicate stent-valve. A self-expanding stent-valve may also have more of a tendency to deform undesirably to a non-circular shape unless the shape is carefully controlled during compression. Further considerations relate to the quantity and bulkiness of accessory equipment that must be taken into an operating theatre merely for preparing or loading a stent-valve into a delivery catheter.

It remains challenging to provide a technique for compressing a stent-valve, that is relatively easy and intuitive to use, inexpensive to implement, uses apparatus that is not too bulky and can conveniently be sterilized, and also avoids the problems discussed above.

The present invention has been devised bearing such issues in mind. It may be a non-limiting object to address and/or alleviate at least one of the above issues.

Certain aspects of the invention are defined in the claims.

Broadly speaking, a further aspect of the invention provides an apparatus for use in compressing a stent (preferably a stent-valve) to a desired size for mounting on a delivery catheter. The apparatus may comprise one or more of:

a hollow channel (which may optionally additionally or alternatively be referred to as a hollow channel member or hollow channel body) having an interior surface shaped for progressively compressing the stent in response to longitudinal advancement of the stent within the hollow channel; and a mover for applying a longitudinal driving force to the stent for advancing the stent within the hollow channel.

Optionally, the apparatus may be configured to have one or any combination of two or more of the following features, which are all optional:

(a) the apparatus further comprises a driver for generating a driving force, the mover being configured to transmit the driving force from the driver to the stent to advance the stent within the channel. The driver may be mounted externally of or on the channel, for example, radially externally or radially outside. The driver may comprise a member rotatable externally around the longitudinal axis of the channel, and a screw thread and/or helical guide for generating longitudinal motion in response to the rotation. For example, the driver may be threadedly coupled to the exterior of the channel. In some embodiments, the channel has (i) a generally cylindrical exterior portion carrying a screw thread for the driver, and/or (ii) a generally non-cylindrical interior portion for collapsing the stent-valve. The generally non-cylindrical interior portion may optionally comprise a substantially round cross-section shape that reduces in diameter progressively along one or more regions of the longitudinal axis.

(b) the hollow channel may comprise at least one slot through a wall thereof, and the mover may comprise a portion slidable in the slot and projecting therethrough for engaging a stent within the channel. The slot may be substantially linear and/or longitudinally extending. Optionally the channel comprises two slots, or optionally the channel comprises three slots, or optionally the channel comprises four slots, or optionally the channel comprises five slots, or optionally the channel comprises six slots, or optionally more. The mover may comprise a corresponding number of said portions, one for each slot. Additionally or alternatively, the hollow channel may comprise a member having at least one slot extending therein. For example, the slot may extend over at least 50% of the axial length of the member, optionally at least 55%, optionally at least 60%, optionally at least 65%, optionally at least 70%, optionally at least 75%, optionally at least 80%, optionally at least 85%, optionally at least 90%, optionally at least 95%. Alternatively, the hollow channel may comprise a plurality of members assembled (or assembleable) together to define the hollow channel form collectively. In either case, the slots may optionally be open at at least one end of the channel, to permit the mover to be separated from the channel by sliding out of the open ends of the slots.

Optionally, the hollow channel comprises a plurality of slots, and the mover comprises (i) a plurality of said portions slidable in slots, and (ii) a portion fitting outside, e.g. radially outside, the channel (e.g. radially outside the circumferential periphery of the channel). The portion fitting outside may interconnect, radially outside the channel, the portions slidable in the slots. For example, the portion fitting outside may connect radially-outer ends of the portions slidable in the slots.

(c) The mover may be configured to apply the longitudinal driving force to at least one (optionally two, or optionally three, or optionally four, or optionally more) circumferential positions around the circumference of the stent. This may enable the driving force to be applied to one or more specific circumferential positions at which the stent (e.g. stent-valve) is relatively robust and/or is less vulnerable to damage or deformation. For example, the one or more circumferential positions to which the force may be applied may be substantially aligned with commissural supports or posts of a stent-valve. Alternatively, the one or more circumferential positions to which the force may be applied may be substantially non-aligned with commissural supports or posts of a stent-valve.

(d) The mover may be configured to apply the longitudinal driving force to at least one (optionally two, or optionally three, or optionally four, or optionally more) longitudinal positions along the axial length of the stent. This may enable the driving force to be applied to one or more specific longitudinal positions at which the stent is relatively robust and/or is less vulnerable to damage or deformation. For example, the one or more longitudinal positions to which the force may be applied may correspond to commissural supports or posts of a stent valve. Additionally of alternatively, each of the one or more longitudinal positions may correspond to a valley in the stent profile or structure (for example a valley defined at a junction of apex between two struts).

(e) The mover may be configured to apply the longitudinal driving force to at least one (optionally two, or optionally three, or optionally four, or optionally more) specific positions that are intermediate the extreme ends of the stent. This may enable a "pushing" force to be applied with less risk of buckling the stent axially. Additionally or alternatively, it may enable a "pulling" force to be applied without relying on or interfering with the extreme ends of the stent. The stent may comprise one or more attachment elements at an extreme end of the stent. Such an arrangement does not interfere with or complicate the engagement by the attachment elements. Additionally of alternatively, each of the positions may correspond to a valley or concavity in the stent profile or structure (for example a valley defined at a junction of apex between two struts). Optionally, the at least one position may be: spaced from both opposite ends of the stent by at least 5 mm, preferably at least 10 mm; and/or spaced from both opposite ends of the stent by at least 10% of a maximum length of the stent-valve, preferably at least 15%.

(f) The mover may comprise a ring extending around the exterior of the channel, and one or more limbs extending or projecting inwardly from the ring. The limbs may be blade-like and/or finger-like and/or pin-like and/or spoke-like. The ring may be slidable longitudinally around the exterior of the channel. Each limb may extend through a respective slot in the channel wall to extend towards the interior of the channel. Each limb may be slidable in the respective slot. The inner ends of the limbs may be substantially free, or the inner ends may be coupled to each other, for example, either meeting at a common point (e.g. centre) or coupled via an inner ring.

(g) The portion or a surface of the mover configured for engagement with the stent (e.g. each limb described above, if used) may extend in a generally radial direction with respect to the channel axis and/or the plane of the ring (if used). Alternatively, the portion or a surface of the mover configured for engagement with the stent may be inclined with respect to the radial direction and/or ring plane. In one form, the portion is inclined in a direction towards an exit and/or narrower (e.g. internally narrower) end of the channel. The angle of inclination (e.g. towards the exit/narrow end) may be about 5° (or more), about 10° (or more), about 15° (or more), or about 20° (or more). The angle of inclination may be between about any two of above values, for example, between about 5° and about 15°. The inclination may reduce the risk of the stent buckling under axial compression loads. The inclination may tend to urge modestly the stent in a radial outward direction instead of radially inwardly. Modest radial outward urging is countered by contact with the interior surface of the channel, thereby enabling the shape of the stent to be controlled to avoid buckling.

(h) The interior surface of the hollow channel may be substantially fixed and/or immovable, at least in a radial direction. The compression of the stent-valve may be achieved at least predominantly (and preferably entirely) as a result of longitudinal displacement of the stent-valve within the channel, without substantial radial movement of the interior surface of the channel.

(i) The interior surface of the hollow channel may comprise at least one non-cylindrical portion, for example, having a diameter that reduces progressively along the longitudinal axis of the channel in a direction towards an exit. Additionally or alternatively, the channel may comprise at least one generally cylindrical portion. In the illustrated embodiments, the interior surface comprises at least two non-cylindrical portions. The portion of the interior surface adjacent to the entrance to the channel may be generally cylindrical. The portion of the interior surface adjacent to the exit of the channel may be generally non-cylindrical.

(j) The apparatus may further comprise a loading tube (which may optionally additionally or alternatively be referred to as a channel extension or an exit extension) for or usable at the exit and/or narrow (e.g. internally narrower) end of the channel. The loading tube may be removably attachable to the channel, or it may be associated with the channel by holding in place by hand, or it may be insertable into the exit of the channel. When the extension is separated (e.g. removed) from the channel, this may permit the end of the stent to be observed at the exit/narrow end of the channel for loading onto, or engagement with, a delivery catheter. After loading/engagement of the stent end to a delivery catheter, the extension may be placed, inserted or re-placed (e.g. attached or reattached) with respect to the channel. In some embodiments, the loading tube has a bore therein. In some embodiments, the bore may have substantially the same diameter as the exit end of the channel. In other embodiments, the bore and/or the outer diameter of the loading tube may be slightly smaller than the diameter at the exit of the channel.

In some embodiments, the loading tube may be attachable by a fixing that withstands longitudinal load between the channel and the extension. For example, the fixing may be a screw threaded fixing. In other embodiments, the loading tube may be insertable at least partly into the channel at or through the exit.

(k) The longitudinal length of the hollow channel may be longer than the stent-valve such that, in use, the stent-valve is contained entirely within the channel when being advanced.

(l) In use, the stent-valve may be passed entirely through the hollow channel from an entrance at one end to an exit at the opposite end.

(m) The stent-valve may be advanced inflow-end first within the hollow channel. The inflow-end may be a first end to emerge from an exit of the hollow channel. Alternatively, the stent-valve may be advanced outflow-end first within the hollow channel. The outflow-end may be a first end to emerge from an exit of the hollow channel.

In a further aspect, the invention provides apparatus for compressing a transcatheter cardiac stent-valve, comprising one or more of: a hollow channel having an interior surface shaped for progressively compressing the stent-valve in response to longitudinal advancement of the stent-valve within the channel; a drive threadedly engaged or engageable on the exterior of the channel for generating a longitudinal driving force in response to rotation; a mover having limbs that project through slots in the channel wall to transmit the driving force to the stent-valve within the channel; and a channel extension removably attachable at the exit to provide a generally cylindrical containment bore.

In a further aspect, the invention provides apparatus for compressing a transcatheter cardiac stent-valve, the apparatus comprising: a hollow channel having an interior surface shaped for progressively compressing the stent-valve in response to longitudinal advancement of the stent within the hollow channel, the hollow channel comprising at least one slot through a wall thereof; and a mover comprising a portion fitting outside the circumferential periphery of the hollow channel and a portion slidable in the slot and projecting therethrough for engaging the stent-valve within the hollow channel, for applying to the stent-valve a longitudinal driving force from outside the hollow channel.

In a further aspect, the invention provides apparatus comprising:
a transcatheter cardiac stent-valve having first and second opposite ends;
a hollow channel having an interior surface shaped for progressively compressing the stent-valve in response to longitudinal advancement of the stent within the hollow channel; and
a mover for engaging the stent-valve within the hollow channel, for applying to the stent-valve a longitudinal driving force from outside the hollow channel, the mover being configured to engage the stent-valve at at least one position intermediate the first and second opposite ends of the stent-valve.

In a further aspect, the invention provides apparatus for compressing a transcatheter cardiac stent-valve, comprising:
a hollow channel having an interior surface shaped for progressively compressing the stent-valve in response to longitudinal advancement of the stent-valve within the hollow channel; and
a driver coupled to the hollow channel by a screw thread, and configured for generating in response to rotation of the driver, a longitudinal driving force for advancing the stent-valve.

In a further aspect, the invention provides apparatus for compressing a transcatheter cardiac stent-valve, comprising:
a hollow channel having an entrance and an exit, the entrance having a larger bore than the exit, the hollow channel further having an interior surface shaped for progressively compressing the stent-valve in response to longitudinal advancement of the stent-valve within the hollow channel, the interior surface comprising at least one selected from:
(i) at least one generally cylindrical surface and at least one generally non-cylindrical surface;
(ii) a plurality of distinct generally non-cylindrical surfaces.

In a further aspect, the invention provides apparatus for compressing a transcatheter cardiac stent-valve, comprising:
a hollow channel having an interior surface shaped for progressively compressing the stent-valve in response to longitudinal advancement of the stent-valve within the hollow channel; and a mover for applying a longitudinal driving force to a stent-valve within the channel, the mover comprising a ring from which extends a plurality of limbs, the limbs extending generally inwardly from the ring, and being inclined with respect to the plane of the ring.

In a further aspect, the invention provides a method of compressing a transcatheter cardiac stent-valve, comprising in any order the steps of:
(a) providing a hollow channel having an entrance and an exit, the hollow channel further having an interior surface shaped for progressively compressing a stent-valve in response to longitudinal advancement of the stent-valve within the channel;
(b) inserting a stent-valve at the entrance of the channel; and
(c) applying from radially outside the channel a longitudinal driving force to advance the stent-valve within the channel towards the exit.

In a further aspect, the invention provides a method of compressing a transcatheter cardiac stent-valve, comprising in any order the steps of:
(a) providing a hollow channel having an entrance and an exit, the hollow channel further having an interior surface shaped for progressively compressing a stent-valve in response to longitudinal advancement of the stent-valve within the channel;
(b) inserting a stent-valve at the entrance of the channel; and
(c) rotating a driver relative to the hollow channel, to generate via a screw thread, a longitudinal driving force for advancing the stent-valve within the channel towards the exit.

In a further aspect, the invention provides a method of compressing a transcatheter cardiac stent-valve, comprising in any order the steps of:
(a) providing a hollow channel having an entrance and an exit, the entrance having a larger bore than the exit, the hollow channel further having an interior surface shaped for progressively compressing a stent-valve in response to longitudinal advancement of the stent-valve within the hollow channel;
(b) providing a loading tube for the hollow channel;
(c) placing the loading tube on to at least a portion of a delivery catheter;
(d) inserting a stent-valve at the entrance of the channel;
(e) applying a pushing force to the stent-valve to advance the stent-valve within the channel towards the exit until a portion of the stent-valve emerges at the exit;
(f) coupling the portion of the stent-valve at the exit to a stent-holder of the delivery catheter;
(g) translating a containment sheath of the delivery catheter to capture there within the portion of the stent-valve coupled to the stent-holder;
(h) moving the loading tube on the delivery catheter to couple the loading tube to the hollow channel and/or insert the loading tube into the exit of the channel; and
(i) applying a further pushing to the stent-valve to further advance the stent-valve towards the exit of the hollow channel.

In a further aspect, the invention provides a method of compressing a transcatheter cardiac stent-valve, the method comprising in any order the steps of:
(a) providing a hollow channel having an entrance and an exit, the entrance having a larger bore than the exit, the hollow channel further having an interior surface shaped for progressively compressing a stent-valve in response to longitudinal advancement of the stent-valve within the hollow channel;
(b) inserting the stent-valve into the entrance of the channel; and (c) applying to the stent-valve at at least one position intermediate opposite ends of the stent-valve, a longitudinal driving force for advancing the stent-valve within the channel towards the exit.

In a further aspect, the invention provides apparatus comprising:
a delivery catheter for delivering a stent-valve to an implantation site within the body, the delivery catheter having at least one translatable sheath at a containment region for receiving the stent-valve in a compressed form as a result of a loading operation for compressing and loading the stent-valve with respect to the delivery catheter; packaging for containing the delivery catheter prior to use, the packaging including a base having a liquid-tight trough, the trough having a depth suitable for use to hold liquid within which the containment region of the catheter may be immersed during the loading operation.

In a further aspect, the invention provides a method of preparing a stent-valve and a delivery catheter for use, the method comprising:
(a) providing a closed packaging containing the delivery catheter, the packaging including a base supporting the delivery catheter in a storage position, the base having a liquid-tight trough;
(b) opening the closed packaging;
(b) introducing liquid into the trough of the base;
(c) loading the stent-valve into a containment region of the delivery catheter while at least the containment region is immersed in the liquid in the trough.

Features and advantages of the invention in its various aspects include one or more of: (i) relatively easy and intuitive to use (ii) inexpensive to implement, (iii) uses apparatus that can conveniently be sterilized, (iv) avoids interfering with an attachment region at one end of the stent, (v) avoids buckling of the stent, (vi) provides accurate control of the stent shape during compression, (v) facilitates loading of the stent on to a delivery catheter, (vi) enables compression of at least a significant portion of the stent to be achieved without stressing engagement with a stent holder of the delivery catheter, (vii) can easily be performed by a single operator, and/or (viii) reduction in the quantity of auxiliary equipment for an operating theatre, by enabling loading/compression in place in device packaging.

Although various features and ideas of the invention are described above and defined in the appended claims, additional features and advantages will become apparent from the following non-limiting description of detailed embodiments. Protection is claimed for any novel feature or idea described herein and/or illustrated in the drawings whether or not emphasis has been placed thereon.

Non-limiting embodiments of the invention are now described by way of example only, with reference to the accompanying drawings, in which:—

FIG. 8 is a schematic side-view of packaging for a delivery catheter, the packing shown with a cover separated from a base;

FIG. 9 is a schematic section similar to FIG. 8;

FIG. 10 is a schematic section along the line A-A of FIG. 8;

FIG. 11 is a schematic section along the line B-B of FIG. 8;

FIG. 12 is a schematic section along the line D-D of FIG. 8;

FIG. 13 is a plan view of the base of the packaging of FIG. 8; and

FIG. 14 is a plan view of the base similar to FIG. 13 but indicating positioning of a delivery catheter in place.

Before describing the compression apparatus in detail, an example stent (stent-valve) is first described so that the features and functions of the compression apparatus may fully be appreciated.

Figure 1:
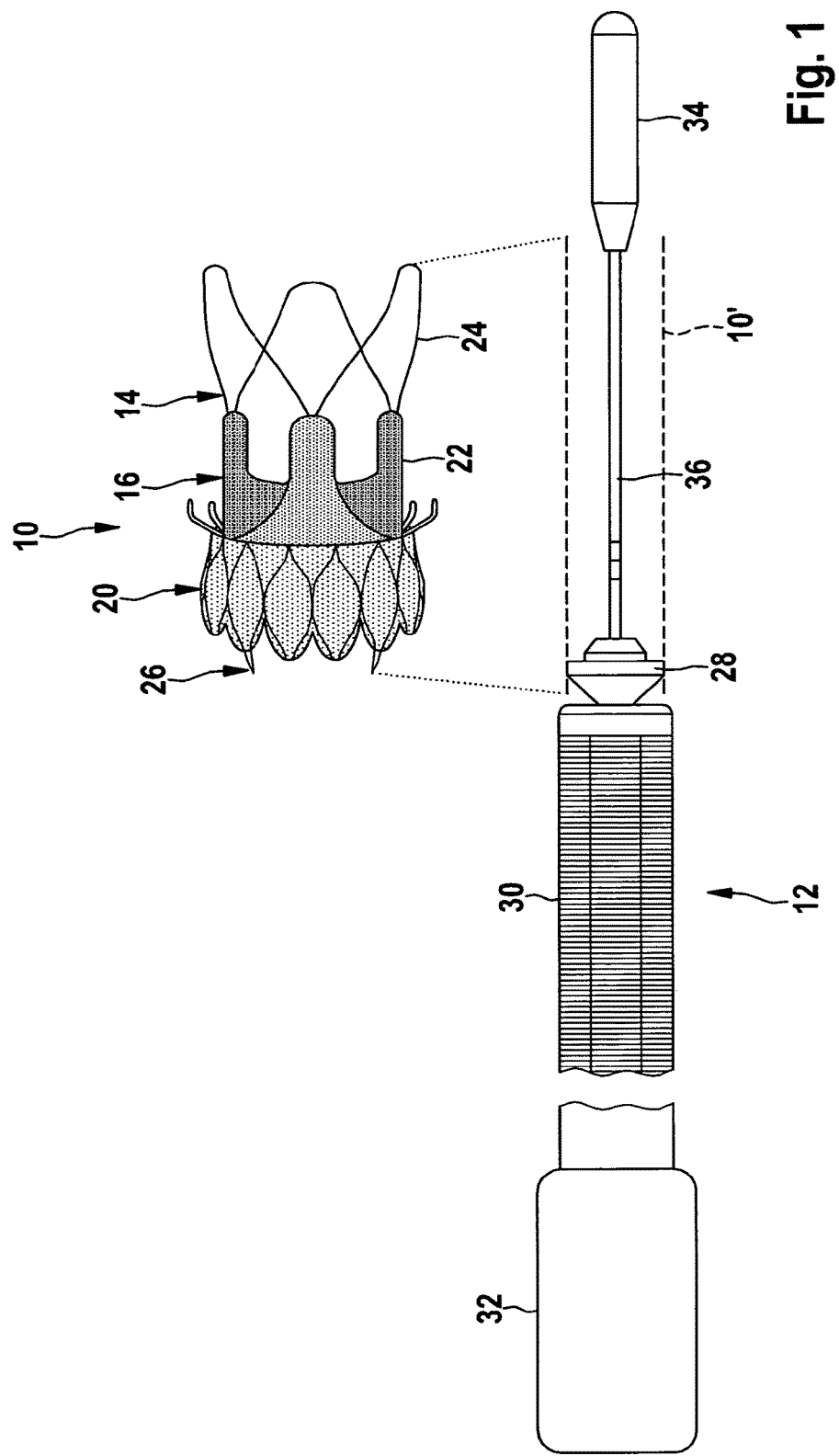
FIG. 1 is a schematic view of an example stent-valve and a delivery catheter therefore.
Figure 2:
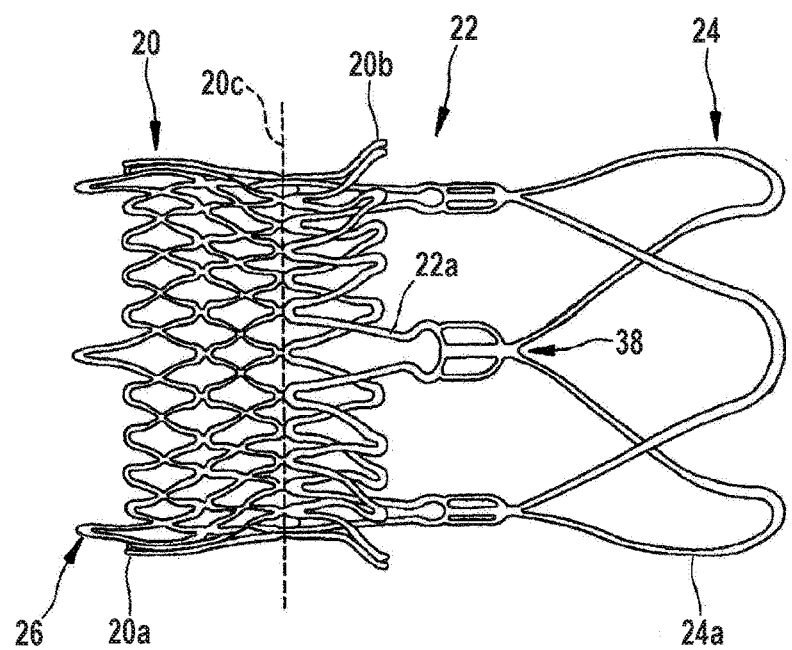
FIG. 2 is a schematic side view of the stent component of the stent-valve of FIG. 1.
Figure 3:
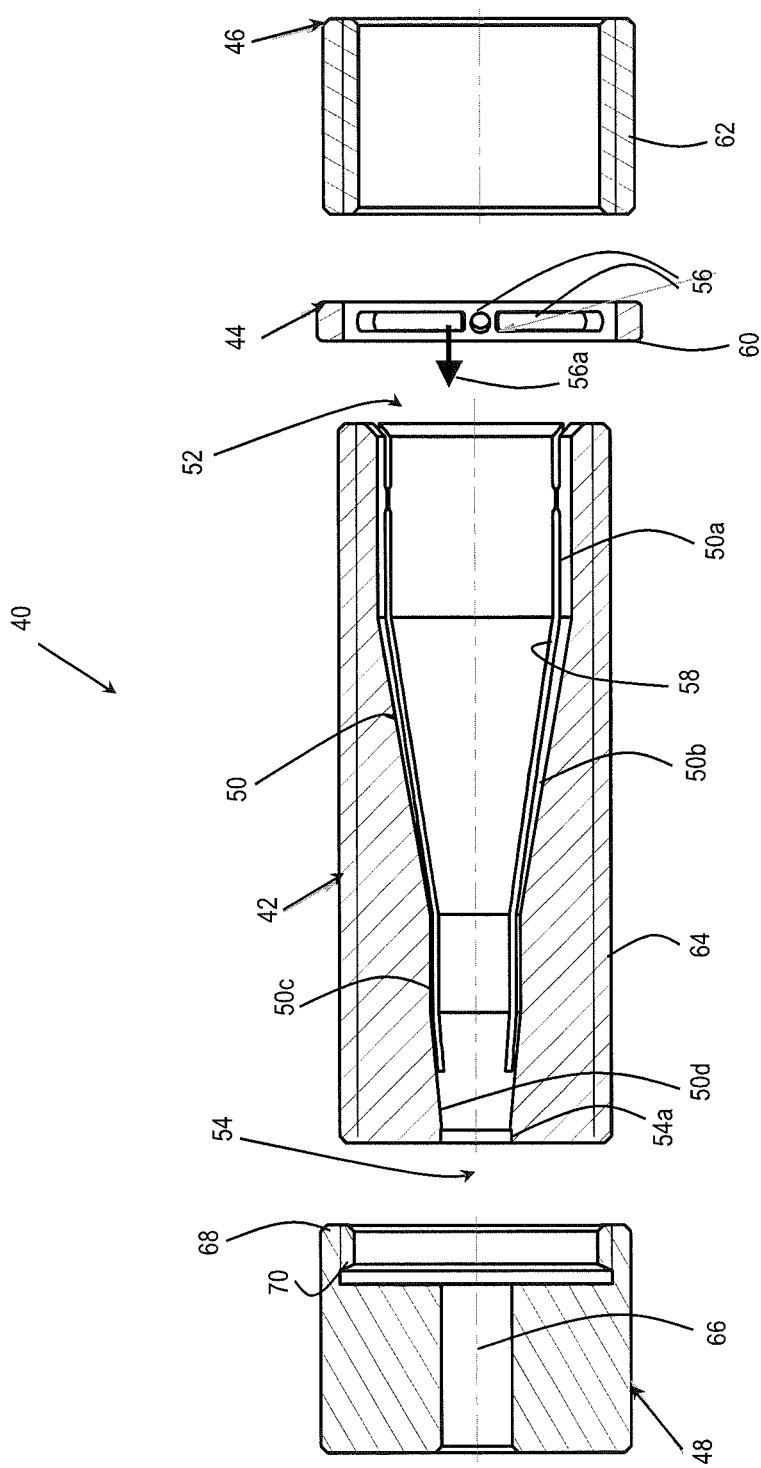
FIG. 3 is a schematic exploded section view of an apparatus for compressing the stent valve for loading on to the delivery catheter.
Figure 4:
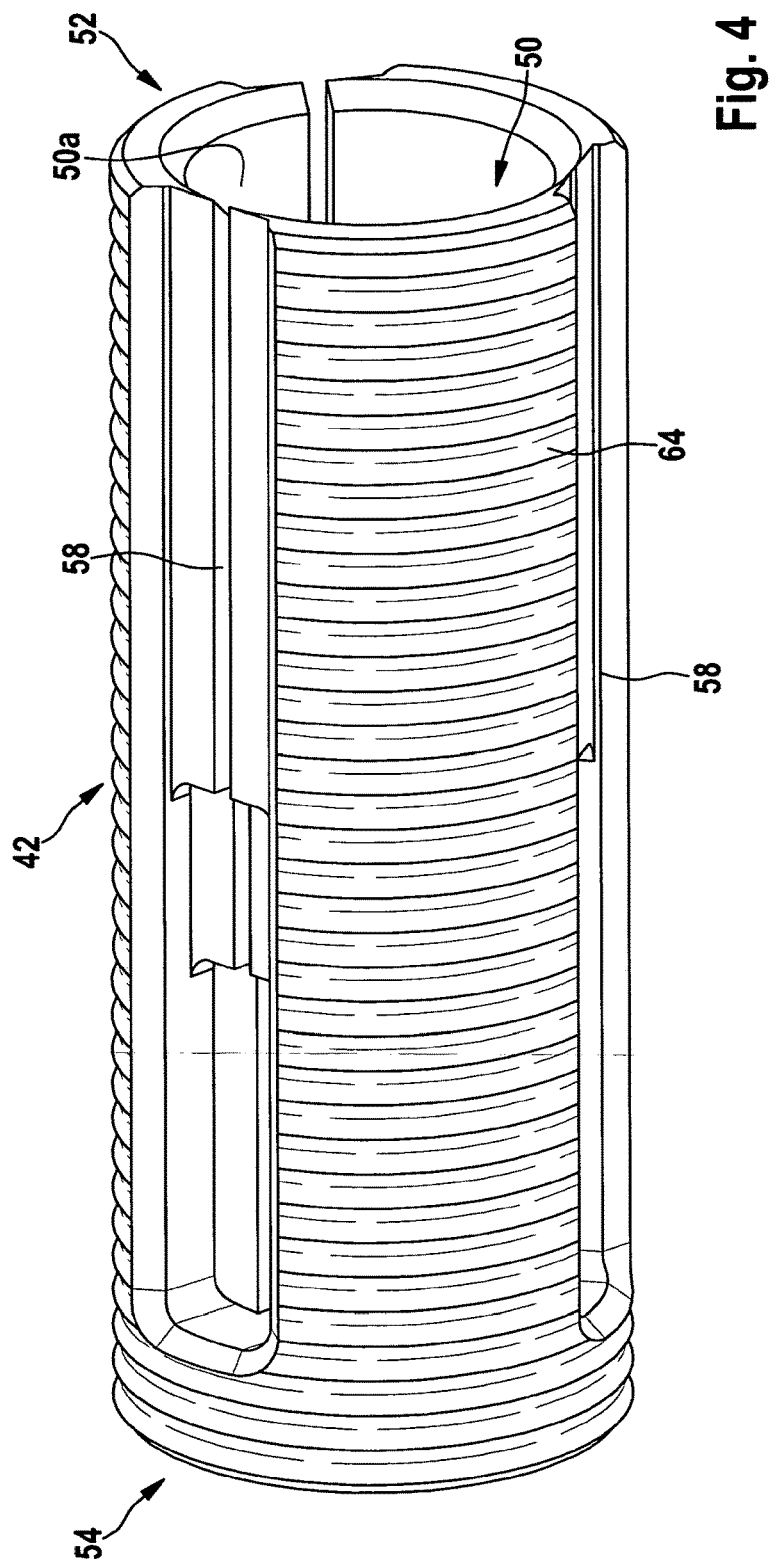
FIG. 4 is a schematic perspective view of the hollow channel of the apparatus of FIG. 3.
Figure 5:
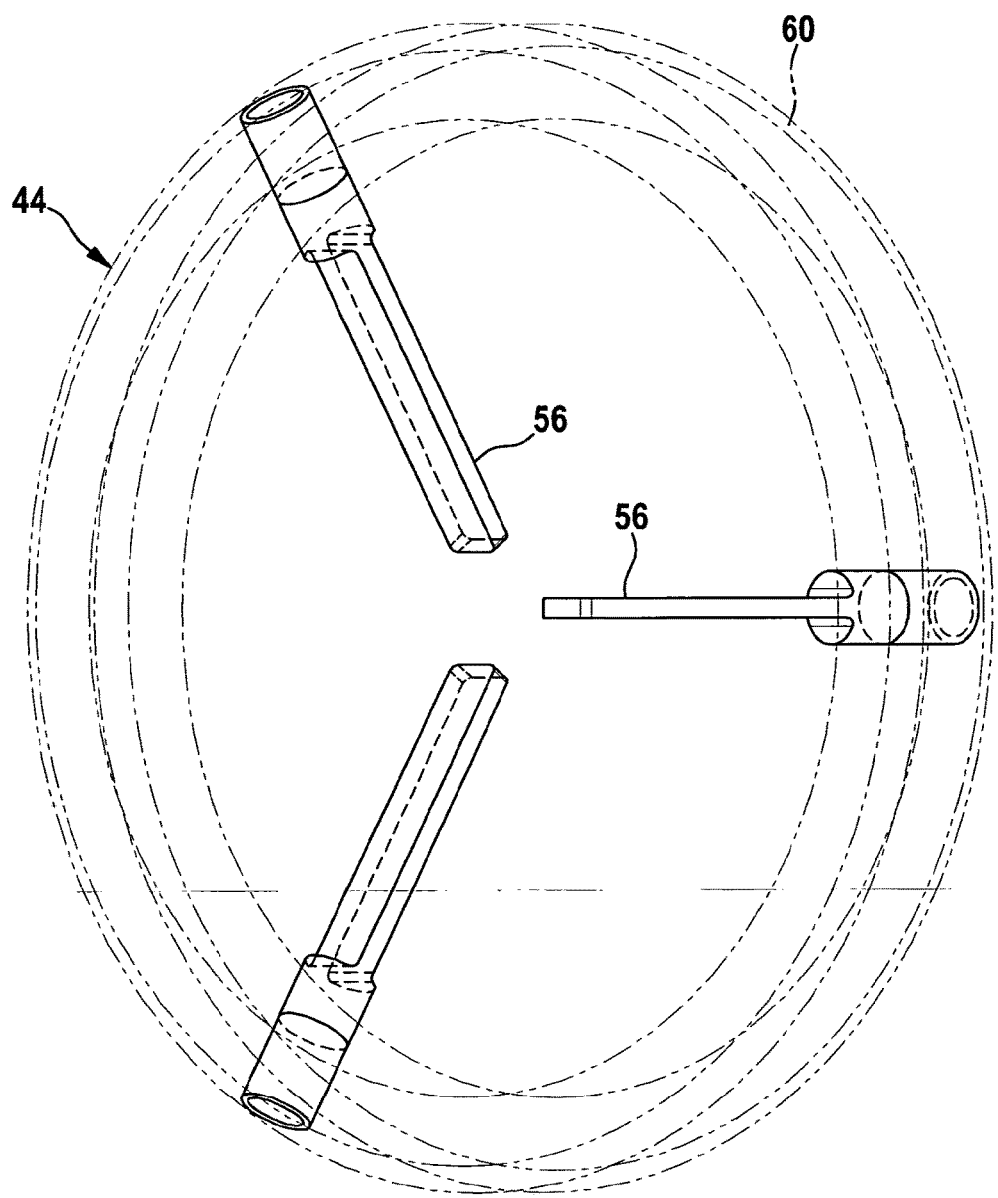
FIG. 5 is a schematic perspective view of the mover of the apparatus of FIG. 3.

FIGS. 1 and 2 illustrate an example stent in the form of a stent-valve 10. The stent-valve 10 may be a cardiac stent-valve, for example an aortic stent-valve. The stent-valve 10 may be configured for transcatheter implantation in the body, for example enabling the use of minimally invasive techniques. The stent-valve 10 may be configured for transcatheter aortic valve implantation ("TAVI"). Although a particular geometry of stent-valve 10 is illustrated by way of example, it will be appreciated that the invention is not limited to any specific stent-valve geometry. The example geometry is used herein because it enables advantages of the invention to be emphasized.

The stent-valve 10 may be transformable between an expanded state (as illustrated in FIG. 1), and a compressed state indicated by the broken line 10'. The expanded state may correspond approximately to an operative state of the stent-valve after implantation. The stent-valve 10 may not fully achieve the expanded state at implantation, tolerance being allowed for size mismatching and/or for slight compression to maintain an outward resilient bias for a friction fit in the native anatomy. The compressed state 10' may correspond to a delivery state to be accommodated by a delivery catheter 12 and/or for introduction into the anatomy to the desired implantation site.

The stent-valve 10 may be of a self-expanding type that is resiliently biased towards the expanded state, and is compressible to the compressed state 10' by application of suitable radial compression forces. The stent-valve 10 remains in its compressed state while constrained. When the constraint is removed, the stent-valve 10 self expands towards the expanded state. Alternatively, the stent-valve 10 may be of a non-self-expanding type that requires application of an expansion force to transform the stent-valve 10 from the compressed state 10' to the expanded state.

The stent-valve 10 may comprise a stent component 14 and a valve component 16. The stent component 14 may provide an anchoring function for anchoring the stent-valve in the native anatomy and/or a support function for supporting the valve component 16. The stent component 14 may be of any suitable material or materials. The stent component 14 may be of metal. Example materials include shape memory and/or superelastic alloys (for example, nitinol), stainless steel, or cobalt-chromium alloy. In the illustrated form, the stent component 14 is self-expanding and is of shape memory/superelastic alloy (e.g. nitinol). However, the stent component 14 could also be substantially non-self expanding.

The stent component 14 may have any profile desired for anchoring and/or aligning the stent-valve 10 with respect to the native anatomy at the desired implantation site. In some embodiments, the stent component 14 may be generally cylindrical in shape, or comprise one more generally cylindrical portions or portions lying on a generally cylindrical surface (e.g. 20c and 22a). Additionally or alternatively, the stent component 14 may be generally non-cylindrical in shape or comprise one or more generally non-cylindrical portions or portions lying on a non-cylindrical surface (e.g. 20a, 20b, and 24). Additionally or alternatively, the stent component 14 may comprise one or more anchor projections, and/or one or more stabilization portions.

In the illustrated from, the stent component 14 optionally comprises an anchoring portion 20 defined, for example, by an inferior crown 20a and a superior crown 20b that define a groove and/or waist 20c therebetween. The anchoring portion 20 may have a first resistance to compression, and may comprise a cellular lattice.

The stent component 14 optionally (further) comprises a valve support portion 22 comprising, for example, a plurality (e.g. three) commissural support posts 22a. The commissural support posts 22a may be arranged on a pitch circle diameter smaller than an extremity of at least one of the crowns 20a and 20b. The commissural support posts 22a may be arranged on a pitch circle diameter corresponding to the waist 20c. The commissural support posts 22a may partly overlap at least one of the crowns 20 and 22 in the axial direction, and extend axially beyond that respective crown. The commissural support posts 22a may be frame-like. The commissural support posts 22a may have a shape that follows, at least approximately, a peripheral contour of the valve, at least in the region of the valve periphery adjacent to the commissural support posts.

The stent component 14 optionally (further) comprises a stabilization or alignment portion 24 defined, for example, by a plurality (e.g. three) wings or arches 24a. The arches 24a may extend from tips of the commissural support posts 22a, to define a vaulted structure thereover. The alignment portion 24 may have a greater flexibility than the anchoring portion 20 and/or the valve support function 22. The alignment portion 24 may have a second resistance to compression that is smaller than the first resistance to compression of the anchoring portion 20. The alignment portion 24 may be less rigid (e.g. radially) than the anchoring portion 20 and/or the valve support portion 22.

The stent component 14 optionally (further) comprises an attachment portion 26 for attaching the stent component 14 to a stent receiver 28 of the delivery catheter 12. In the illustrated embodiment, the stent receiver 28 may be a stent holder and will be referred to as such hereinafter, although other types of receiver for receiving and/or accommodating at least a portion of the stent-valve 10 may be used as desired. The attachment portion 26 may comprise one or more geometrical openings, or one or more lugs or other projections, for forming an interference (e.g. interlocking) fit with a complementary portion of the stent holder 28. The attachment portion 26 may be arranged at or adjacent to at least one extreme end of the stent component 14. In the present embodiment, the attachment portion 26 is defined by a plurality (e.g. three) of extensions of cells of the inferior crown 20a.

The valve component 16 may be of any suitable natural and/or synthetic material(s). For example, the valve component 16 may comprise porcine and/or bovine pericardium and/or harvested natural valve material. The valve component 16 may comprise a plurality of leaflets arranged to coapt or collapse to a closed position to obstruct flow in one direction therepast, while flexing apart to an open position to allow flow in an opposite direction. The valve component 16 may be accommodated at the valve support portion 22 and/or at least partly within the anchoring portion 20. The stent-valve 10 (e.g. the valve component 16) may further comprise an inner skirt and/or an outer skirt covering at least partly a respective inner or outer surface portion of the stent component 14. For example, the skirt(s) may cover at least a portion of the anchoring portion 20 and/or at least a portion of the valve support portion 22.

Still referring to FIG. 1, the delivery catheter 12 may by way of example only, comprise at least one sheath 30 at a containment region of the delivery catheter 12, for accommodating a stent-valve 10. The at least one sheath 30 may be configured for covering at least a portion of the stent-valve 10 in its compressed state 10', for constraining the stent-valve 10 against expansion. The at least one sheath 30 is translatable along the axis of the catheter to selectively cover or expose the respective region of the stent-valve 10, in response to actuation by a control at a handle end 32 of the delivery catheter 12. The stent holder 28 may prevent, or at least reduce, any tendency of the stent-valve 10 to displace axially during translation of the sheath 30, and/or prevent, or at least reduce, any tendency of the stent-valve 10 to jump free of the sheath 30 when only a small portion of the stent-valve 10 is covered by the sheath 30. The stent holder 28 may be carried on a central tube 36 (or an assembly of plural tubes), for example, for receiving a guide-wire. A loading tip 34 may be removably mounted at the most distal end of the tube 36. Other designs of delivery catheter 12 may be used, for example, without a sheath 30 and/or without a stent holder 28. The example delivery catheter 12 is used herein because it enables advantages of the invention to be emphasized.

The maximum outer diameter of the stent-valve 10 in its expanded state may be from about 25 mm to about 35 mm. In contrast, the maximum outer diameter of the stent-valve in its compressed condition 10' for the delivery catheter may be significantly smaller, for example about 10 mm or less. The radial force required to be applied to compress the stent-valve may be considerable, for example, at least 50 N, or at least 75 N, or at least 100 N. In some embodiments, the radial force is between about 100 N and 120 N.

Referring to FIGS. 3-7, apparatus 40 is illustrated for compressing the stent valve 10 to its compressed state 10'. The apparatus 40 is also configured to facilitate loading of the stent-valve 10 on to the delivering catheter 12 as part of the compression process.

The apparatus 40 may comprise one or any combination of two or more of the following components: a hollow channel (or hollow channel member or hollow channel body) 42; a mover 44; a driver 46; a loading tube (or channel extension) 48. Some or all of the components 42-48 may be disassemblable from each other, and assembled during use of the apparatus 40.

The hollow channel 42 may have an interior surface 50 shaped for progressively compressing the stent-valve 10 in response to longitudinal advancement of the stent-valve 10 within the channel 42 from an entrance 52 at one end to an exit 54 at the opposite end. The interior surface 50 may be generally round in cross-section, in order to maintain the round shape of the stent-valve 10 during compression. The interior surface 50 may comprise one or more non-cylindrical portions 50*b* and 50*d*, for example, having a diameter that reduces progressively (e.g. converges) along the longitudinal axis of the channel 42 in a direction towards the exit 54. Such a shape may be referred to as a funnel shape. The funnel may be straight sided or concave or convex in profile. The interior surface 50 may further comprise one or more generally cylindrical portions 50*a* and 50*c*. The interior surface 50 may be coated to reduce the friction between the surface 50 and the stent-valve 10 e.g. with a hydrophobic silicone based coating.

In the illustrated embodiment, a generally cylindrical portion 50*a* is provided adjacent to the entrance 52 of the channel 42. The cylindrical portion 50*a* may facilitate initial insertion of the stent-valve 10 into the channel 42 without substantial compression (and in the case of a self-expanding stent-valve, without any tendency for the stent-valve to spring back out of the entrance 52). Additionally or alternatively, a generally non-cylindrical portion 50*d* (e.g. funnel shaped) may be provided adjacent to the exit 54 of the channel 42. The non-cylindrical portion 50*d* may promote a convergent (e.g. conically tapered) shape at the end of the stent-valve 10 when emerging at the exit 54, to facilitate engagement of the stent-valve 10 with the stent holder 28 of the delivery catheter 12 during loading.

The exit 54 of the channel 42 may optionally be formed with an annular step socket 54*a* for receiving the tip of a sheath 30 of the delivery catheter 12, to facilitate loading into the sheath 30. The socket 54*a* may have an inner diameter matching substantially the outer diameter of the (e.g. distal) end of the sheath 30 to be received therein.

The wall(s) of the channel 42 may be generally stationary or fixed, at least in a radial direction. Compression of the stent-valve 10 is achieved by advancing the stent-valve 10 within the channel 42, such that the stent-valve 10 bears against the interior surface 50 and is forced to compress in order to advance therealong and/or therepast.

The mover 44 may be configured for applying a longitudinal driving force generated outside the channel 42, to the stent-valve 10 within the channel 42, in order to advance the stent-valve 10 within the channel 42. The mover 44 may be configured for applying the longitudinal driving force from radially outside the channel 42, to the stent-valve 10, in order to advance the stent-valve 10 within the channel 42. The mover 44 may comprise one or more portions (e.g. limbs) 56 that slide in respective slots 58 in the wall of the channel 42, and project from outside the channel 42 through the slots 58 into the interior of the channel 42. The (limb) portions 56 are configured for engaging portions of the stent-valve 10 to advance the stent-valve 10 as the mover 44 is driven to translate longitudinally.

Applying the driving force using such a mover 44 may enable the driving force to be applied to the stent-valve at one or more positions that are intermediate the opposite ends of the stent. This may enable a "pushing" force to be applied with less risk of buckling the portion of the stent under axial compression load. Additionally or alternatively, it may allow a force ("pulling" or "pushing") to be applied without interfering with the extreme ends of the stent, nor relying on or using the attachment portion 26.

Alternatively, the mover 44 may enable the driving force to be applied at an extreme end of the stent-valve 10, yet solve the problem of how to advance a stent-valve (i) through a hollow channel that is longer than the stent-valve and/or (ii) applying a pushing force to a portion of the stent-valve that itself becomes compressed.

Additionally of alternatively, applying the driving force using such a mover 44 may enable the driving force to be applied at one or more positions (radial and/or longitudinal) at which the stent is relatively robust and/or is less vulnerable to damage or deformation.

Figure 7:
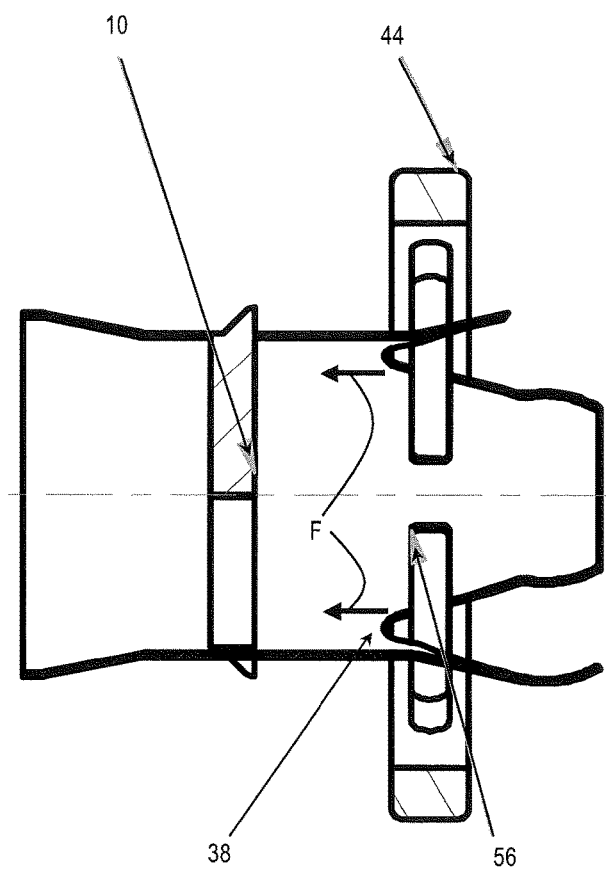
FIG. 7 is a schematic side view of the mover engaging the stent-valve to apply a driving force thereto (other components being omitted in FIG. 7 to avoid obscuring the view)

In the present example, the driving force is intended to be applied to the commissural support posts 22*a* (see FIGS. 2 and 7). The driving force "F" may be applied at the junctions between the commissural support posts 22*a* and the alignment arches 24*a* connected to each respective post 22*a*. The driving force may be applied in the hollow 38 (also referred to as a valley or concavity) between two adjacent arches 24*a*. Using such a technique, the mover 44 can contact the stent-valve 10 at a position that is (i) clear of the valve component and the skirt(s), in order to avoid damage thereto, and/or (ii) clear of the lattice structure of the anchor portion 20 that is densely packed during compression. The commissural support posts 22*a* may provide robust support for receiving the driving force, stronger than for example the stabilization portion 24.

The (limb) portions 56 may have any suitable shape and configuration desired for engaging the stent-valve 10. In the illustrated form, each limb portion 56 is generally rectangular and/or generally planar in cross-section shape. The limb portion 56 may have a blade form. The cross-section shape may provide a relatively thin and/or flat surface contacting the stent-valve 10. The cross-section shape may define a first dimension contacting the stent-valve 10 that is smaller than a dimension of the shape that is generally transverse to the first dimension.

Such a shape or shapes may reduce any tendency for the limb portion 56 to wedge open a space in the stent-valve 10, while still providing the limb portion 56 with adequate bending strength to transmit the driving force cantilever-wise to the stent-valve 10 through the slots 58.

In the form illustrated in the drawings, the limbs 56 extend inwardly in a generally radial direction (e.g. perpendicular to the longitudinal axis of the channel 42). Alternatively, each limb portion 56 may be inclined relative to the radial direction. The angle of inclination may be about 5° or more, optionally about 10° or more, optionally about 15° or more or optionally about 20° or more. Additionally or alternatively, the angle of inclination may be not more than about 30°, optionally not more than about 25°, optionally not more than about 20°, optionally not more than about 15°, optionally not more than about 10°. The limb portions 56 may be inclined in a direction towards the exit 54 of the channel 42 when the mover 44 is mounted thereon (such that the inner tips of the limb portions 56 incline towards the exit 54, as indicated by arrow 56*a* in FIG. 3). Such an arrangement may prevent, or at least reduce, any tendency for the stent-valve to buckle inwardly during compression. Instead, the inclination biases the stent-valve modestly outwardly towards the surface 50, the presence of the surface 50 obstructing outward buckling. In other embodiments, a different angle of inclination and/or a different direction of inclination may be used. In yet other embodiments, the limbs 56 may extend inwardly in a substantially radial direction.

In the illustrated form, the radially inner tips or ends of the limb portions 56 are free and define a clearance therebetween. The clearance enables a distal portion of the delivery catheter 12 to be accommodated as the stent-valve 10 is loaded on to the delivery catheter 12 as part of the compression process. In other forms, the inner ends of the limb portions 56 may be coupled together.

The mover 44 may optionally further comprise a ring 60 that carries the limb portions 56, and/or from which the limb portions 56 extend. The ring 60 may fit around the outside of the channel 42, and be slidable longitudinally along at least a portion of the length of the channel (e.g. slidable along at least a portion corresponding to the extent of the slots 58). The slots 58 may be open at at least one end of the channel 42 (e.g. the entrance 52) to enable the mover to be disengaged from the channel 42 for introducing a stent-valve 10 at the entrance.

The channel 42 may be made substantially as a single member having the slots 58 formed therein (as illustrated in the preferred embodiment). Alternatively, the channel 42 may comprise a plurality of component parts that are assemble together to define collectively the channel form.

In some embodiments, the mover 44 may be driven directly by hand, but in the preferred embodiments, the driver 46 may provide additional convenience and control for generating and applying (e.g. homogenously) a driving force for the mover 44.

The driver 46 may be movable with respect to the channel 42 and be coupled (or couplable) to the channel 42 for generating the driving force in response to relative movement applied to the driver 46. The driver 46 may be external to the channel 42. For example, the driver 46 may comprise a rotary member 62 rotated by hand or by using a suitable tool. The rotary member 62 may be rotatable around the longitudinal axis of the channel 42. The rotary member 62 may be coupled (or couplable) to the channel 42 by means of a screw thread 64 and/or a helical guide, in order to generate longitudinal displacement in response to rotation of the rotary member 62. The driver 46 (e.g. the rotary member) bears directly or indirectly against the mover 44 (e.g. against the ring), to apply the driving force thereto as the rotary member 62 is rotated. The (limb) portions 56 transmit the driving force to the stent-valve 10 to advance the stent-valve 10 within the channel 42.

In the illustrated form, the channel 42 has a generally cylindrical exterior portion carrying the screw thread 64 for the rotary member 62. The rotary member 62 may be unscrewed and disassembled from the thread 64, for example, at the entrance 52 of the channel 42. Such unscrewing/disassembly permits removal of the mover 44 for insertion of the stent-valve into the entrance 52 of the channel 42, and subsequent refitting of the mover 44 and the rotary member 62.

The loading tube (or channel extension) 48, if provided, may comprise a bore 66. The bore 66 may correspond in diameter to the exterior diameter of the sheath 30 of the delivery catheter and/or to the diameter of the socket 54a. In the illustrated form, the loading tube 48 further comprises a lip 68 carrying a fixing 70 for removably attaching the extension 48 to the channel 42 with the bore 66 aligned substantially with the channel exit 54. The fixing 70 may be a female screw thread for threadedly engaging the screw thread 64 of the channel 42, for example, at the exit end of the channel 42. In other embodiments, a different fixing 70 may be used for removably attaching the loading tube 48 to the channel 42. In yet other embodiments, no fixing may be used, and the loading tube 48 instead may be held in place when desired by hand, or by some other external holder. In yet other embodiments, the loading tube may be dimensioned to be insertable at least partly within the exit of the channel 42.

The loading tube 48, if provided, may simplify coordination between the delivery catheter 12 and the channel 42. The loading tube 48 may reinforce the sheath 30 and/or permit compression of at least a portion of the stent-valve 10 into the loading tube 48 prior to capturing of that portion of the stent-valve by the sheath. Optionally, the loading tube 48 may be slid over the sheath 30. The loading tube 48 may be slid back (away from the channel 42) to facilitate loading engagement between the attachment portion 26 and the stent holder 28. Thereafter, the loading tube may be slid forward (towards the channel 42) to reinforce the sheath 30 and/or to permit compression of the stent-valve 10 into the extension 48 without having to continuously adjust the sheath 30 to collect the progressive compression of the stent-valve 10.

The above components may be made of any suitable material or materials, including metal and/or plastics and/or ceramics. Merely by way of example, the channel 42, the driver 46, and the loading tube 48 may of plastics; and/or the ring 60 of the mover 44 may be of metal; and/or the limbs 56 of the mover 44 may be of plastics (e.g. to avoid metal-metal contact with the stent component 14). In other forms, the limbs 56 could be of metal or ceramics, either optionally being coated or carrying a cover of plastics. Alternatively, the ring 60 and the limbs 56 of the mover 44 could be of plastics, e.g. integrally moulded together.

The loading tube 48 and/or the channel 42 may optionally be transparent or translucent to enable the operator to see the state of the stent-valve 10 during compression, and to aid loading and manipulation of the delivery catheter 12.

Figure 6:
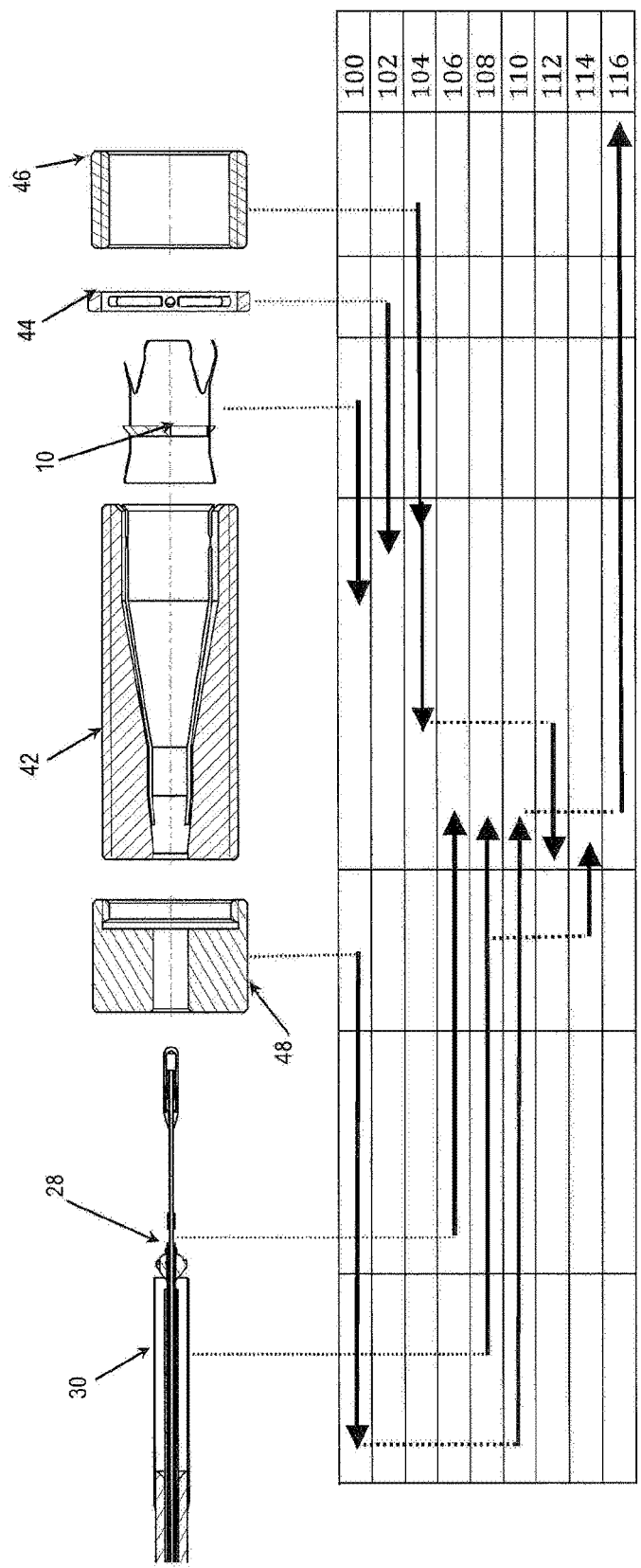
FIG. 6 is a schematic guide to one example of using the apparatus.

An example compression and/or loading process is now described by way of example only with respect to FIG. 6, in which relative directions of movement of components may be indicated by the sequence of arrows.

At step 100, the loading tube 48 if provided, may be slid over the sheath 30 while separated from the channel 42. The loading tube 48 may be slid back towards the handle end (32) so that the loading tube 48 does not cover the stent holder 28. The sheath 30 may be translated back also to expose the stent holder 28.

Still at step 100, prior to inserting the stent-valve 10 in the channel 42, the driver 46 may be unscrewed and separated from the channel 42. The mover 44 may be slid out of the open ends of the slots 58 at the entrance 52. Thereafter, the stent-valve 10 may be inserted by hand into the entrance 52. The stent-valve 10 may be inserted with the end including the attachment portion 26 first. In the present example, the end inserted first includes the anchoring portion 20 and/or the inferior crown 20a thereof. The stent-valve 10 is orientated rotationally such that the portion(s) of the stent-valve 10 to which the driving force is to be applied by the mover, are aligned substantially (or at least roughly) in register with the slots 58. In the present example, these portions correspond to the commissural support posts 22a. The generally cylindrical interior surface portion 50a at the entrance 52 enables the stent-valve 10 to be inserted relatively easily, without substantial compression initially.

At step 102, the mover 44 may be re-placed at the entrance 52, such that the ring 60 fits outside the channel 42, and the limbs 56 are received in the slots 58 and engage the tips of the commissural support posts 22a (illustrated in FIG. 7).

At step 104, the driver 46 may be placed over the ring 60 of the mover 44 at the entrance 52, and rotated to threadedly engage the screw thread 64, and retain the stent-valve 10 and the mover 44 relative to the channel 42.

Thereafter (still at step 104), continued rotation of the driver 46 relative to the channel 42 generates a longitudinal driving force that is applied to the stent-valve 10 via the mover 44, to advance the stent-valve 10 towards the exit 54. As the stent-valve 10 advances, the contact with the non-cylindrical portion(s) 50b and 50d of the interior surface 50 compresses the stent-valve 10 progressively towards the compressed state. As the stent-valve 10 approaches the exit 54, the attachment portion 26 may emerge first at the exit end 54.

At step 106, the distal end of the delivery catheter may be introduced into the exit end 54 (if not already in position, as explained below), until the stent holder 28 engages and/or mates with the exposed attachment portion 26. The ability to see the exposed attachment portion 26 projecting from the exit end 54 of the channel facilitates the task of engaging the attachment portion 26 with the stent holder 28. The provision of the non-cylindrical portion 50d of the interior surface 50 at the exit 54 encourages the attachment portion 26 projecting from the exit 54 to adopt a convergent shape, also to facilitate engagement with the stent holder 28. In some cases, the distal end of the delivery catheter may be introduced into the exit end 54 at an earlier stage, so that it is already in place ready to receive the attachment portion 26, or it may be introduced once the attachment portion 26 begins to arrive at the exit end 54 prior to emerging therefrom.

At step 108, the sheath 30 may be translated distally in order to cover the attachment portion 26 attached to the stent holder 28, and thereby capture the end of the stent-valve 10.

Thereafter, the further steps of the compression and/or loading process may depend on whether the loading tube 48 is used. If the loading tube 48 is not used, the process may progress incrementally by step-wise rotation of the driver 46 (step 112) to advance the stent-valve 10 a short distance, followed each time by corresponding (distal) translation of the sheath 30 towards the exit 54 (step 114) to progressively capture the portion of the stent-valve newly exposed at the exit. Each time, the sheath 30 may be translated until contact within the socket 54a.

Alternatively, if the loading tube 48 is used, at step 110 the loading tube 48 may be slid along the sheath into contact with the exit end 54 of the channel 42. The loading tube 48 may be attached to the channel 42 (e.g. using the fixing 70), or held in place by hand. The loading tube 48 may provide reinforcement or containment to obviate or reduce any need to further translate the sheath 30 step-wise as the stent-valve 10 further emerges at the exit end 54 of the channel 42. Instead, at step 112, the driver 46 may be rotated to advance the stent-valve 10 towards full compression, without further translating the sheath 30. The sheath 30 may remain covering merely the attachment portion 26 attached to the stent holder 28. The sheath 30 may displace away from the exit 54, while all the while remaining contained within the loading tube 48. The loading tube 48 may temporarily contain the compressed stent-valve 10 in a cylindrical or near cylindrical compressed state. Once the mover 44 has reached a final position at the end of the slots 58 near the exit 54, at step 114 the sheath 30 may be translated again towards the exit end 54 of the channel 42 in order to capture, within the sheath, the portion of the stent-valve 10 contained by the loading tube 48. It may be appreciated that the amount of additional compression required for the stent-valve to pass from the bore 66 of the loading tube 48 and into the sheath 30 is relatively small, and may easily be accomplished by translation of the sheath 30 within the loading tube 48. The loading tube 48 surrounding the sheath 30 may reinforce the sheath 30 should reinforcement be necessary.

Using either technique, the stent-valve 10 is attains a substantially compressed state in which at least a majority of the anchoring portion 20 (and optionally at least a portion of the valve support portion 22) is/are compressed and loaded within the sheath 30. The stabilization portion 24 of the stent-valve 10 may remain within the channel 42. At step 116, the apparatus 40 is disengaged from the delivery catheter 12 and the stent-valve 10 by sliding the apparatus 40 distally off the delivery catheter 12. At least a portion of the stabilization portion 24 of the stent-valve 10 that may not have previously left the hollow channel 24 may tend to re-expand because that portion 24 is not constrained by the sheath 30. However, the stabilization portion 24 is relative flexible in a radial direction, and can be compressed later easily without the need for the hollow channel 42, as explained below.

Final stages of the loading process (not illustrated in FIG. 6, because these are not related directly to the apparatus 40) may include one or more of:
  (i) removing the loading tip 34 of the delivery catheter 12 and replacing by an implantation tip; and
  (ii) translating the sheath 30 further distally to compress the stabilization portion 24. The sheath 30 may be translated into contact with the delivery tip, to close the distal region of the delivery catheter 12 ready for use for implantation.

FIGS. 8 to 14 illustrate example packaging 120 in which the delivery catheter 12 may be stored, transported, and supplied to a site at which the delivery catheter 12 is to be used. The position of the delivery catheter 12 is illustrated in FIG. 14. The packaging 120 optionally also contains apparatus 40 (in FIGS. 9, 10, 13 and 14) for compressing and/or loading a stent-valve 10. The apparatus 40 may be, or comprise, any of the features of the above-described embodiments.

The packaging 120 generally comprises a base 122 and a cover (e.g. lid) 124 for covering the base 122 to close the packaging 120. The base 122 comprises a trough 126 for receiving, at least partly, the delivery catheter 12. In the illustrated embodiment, the trough 126 is dimensioned to be able to accommodate substantially the entirety of the delivery catheter 12.

A feature of this embodiment may be that the trough 126 is generally liquid tight, and is usable for holding a liquid within which the stent-valve 10 and/or a containment region 12a of the delivery catheter 12 is immersed during an operation to compress and/or load the stent-valve 10 with respect to the delivery catheter 12. Optionally, a further feature may be that the same trough 126 is used to hold the delivery catheter 12 in (i) a storage position in the packaging 120 in which the delivery catheter 12 is initially supplied, and (ii) a loading position for loading the stent-valve 10 on the delivery catheter 12. Optionally, the storage position and the loading position may be substantially the same as each other. In at least one of the positions (or both positions, as appropriate), the delivery catheter 12 may be substantially parallel with a plane of the base, and/or substantially horizontal when in use for loading a stent-valve. Arranging the delivery catheter 12 substantially parallel to the plane of the base can enable the height of the packaging to be kept desirably small. Arranging the delivery catheter 12 substantially parallel to the plane of the base and/or substantially horizontal in use during loading of a stent-valve, can (i) enable the amount of liquid needed to fill the trough to be kept desirably small, and/or (ii) reduce the amount of air that may inevitably become trapped within the delivery catheter during the loading operation. Trapped air should be removed prior to insertion of the catheter into the patient's body, and reducing the amount of air likely to be trapped during loading can ease the burden of such a subsequent "de-airing" step.

The trough 126 may be a uniform depth, or it may have a depth that varies along its length. At least in a region 126a within which the stent-valve 10 is compressed and/or loaded, or the containment region 12a of the delivery catheter 12 is accommodated, the trough 126 has a depth greater than the transverse dimension of the stent-valve 10 and/or the loading apparatus 40. For example, the depth in the region 126a may be: at least 1 cm; at least 2 cm; at least 3 cm; at least 4 cm; at least 5 cm; at least 6 cm; at least 7 cm; at least 8 cm; at least 9 cm; at least 10 cm; at least 11 cm; at least 12 cm; at least 13 cm; at least 14 cm; at least 15 cm.

The trough 126 may have a uniform width, or it may have a width that varies along its length.

In some embodiments, the trough 126 includes one or more first surface portions 128 that together define a socket that fits a form of portions of the delivery catheter 12 to cradle the catheter against substantial movement. Additionally or alternatively, the trough 126 includes or more second surface portions 130 that together define clearances 130a adjacent to portions 12b of the delivery catheter that are intended to be manually gripped or accessed to manipulate the catheter and/or translate the sheath. Additionally or alternatively, the trough 126 includes one or more surface portions 130 defining a clearance for the region 126a. In some embodiments, the trough 126 includes the one or more first surface portions 128 and the one or more second surface portions 130, such that the second surface portions 130 permit manual access to manipulate the sheath while the delivery catheter 12 is in the position defined by the first surface portions 128.

The base of the trough 126 may be generally flat (optionally with rounded corners) and/or at least portions of the base of the trough 126 may be shaped to cradle or cup the delivery catheter and/or the loading apparatus from below.

The liquid capacity of the trough 126 may be chosen by design. In some embodiments, the liquid capacity may be such that (optionally with the delivery catheter 12 and/or the loading apparatus 40 in place within the trough 126) the amount of liquid for the trough 126 may be one or more selected from: not more than 4 liters; not more than 3.5 liters; not more than 3.25 liters; not more than 3 liters; at least 1 liter; at least 2 liters. For example, the amount of liquid may be measured when both the delivery catheter 12 and the loading apparatus 40 are placed within the trough 126.

The cover 124 optionally comprises one or more projections 132, such as one or more ridges, that depend from the cover 124 and mate with the trough 126 and/or engage (i) the delivery catheter 12 and/or (ii) the loading apparatus 40, to retain the delivery catheter/loading apparatus captive within the trough. The projections 132 may have a profile 134, such as a concave shape, configured to cup the surface of the delivery catheter/loading apparatus.

The loading apparatus 40 may optionally be contained within a compartment distinct from the trough 126, or it may be contained in a region 136 of the trough 126 reserved therefor. As explained above, the loading apparatus 40 may be restrained in place by the cover 124 (or a projection 132 of the cover).

The base 122 may further comprise one or more compartments distinct from the trough 126, for containing accessories.

The base 122 and/or the cover 124 may be of any suitable material or materials, for example, plastics. The base 122 and/or the cover 124 may be formed by any suitable technique, for example, blow molding or injection molding.

Example steps for using the packaging 120 may include, in any order, one or more of the following:

(a) providing the packaging 120, in closed form, containing the delivery catheter 12 and/or the loading apparatus;
(b) opening the packaging 120 (e.g., removing the cover 124);
(c) introducing liquid into the trough 126; and
(d) loading a stent-valve into a containment region 12a of the delivery catheter 12 while at least the stent-valve and/or the containment region 12a is immersed in the liquid in the trough. For example, the apparatus 40 may be placed on to the tip of the delivery catheter 12, and manipulated within the region 126a of the trough 126.

The liquid may, for example, be saline. The liquid may be colder than body temperature. For example, the liquid may be at about room temperature.

The step (d) may be carried out with the delivery catheter 12 substantially horizontal.

The method may further include a step of removing trapped air from the delivery catheter 12 after the loading operation (e.g. a "de-airing" step). As explained above, carrying out step (d) with the delivery catheter substantially horizontal may reduce the quantity of air trapped during the loading operation.

The step (d) may include the steps described above in relation to FIG. 6 of the drawings.

The foregoing description is merely illustrative of preferred embodiments of the invention and does not limit the scope of protection. Many equivalents, modifications and improvements may be used within the scope of the invention.

The invention claimed is:

1. An apparatus for compressing a transcatheter cardiac stent-valve, the apparatus comprising:
   a hollow channel having an interior surface shaped for progressively compressing the stent-valve in response to longitudinal advancement of the stent within the hollow channel, the hollow channel comprising at least one slot through a wall thereof; and
   a mover comprising a portion fitting outside the circumferential periphery of the hollow channel and a portion slidable in the slot and projecting therethrough for engaging the stent-valve within the hollow channel, for applying to the stent-valve a longitudinal driving force from outside the hollow channel;
   wherein the portion of the mover slidable in the slot is shaped as a blade having a thin leading edge or surface that advances within the slot, and a long edge or surface that slides against the edge of the slot.

2. The apparatus of claim 1, wherein the hollow channel comprises a plurality of said slots, and wherein the mover comprises a corresponding number of portions slidable in the slots and projecting therethrough for engaging the stent-valve within the channel.

3. The apparatus of claim 2, wherein the portion of the mover fitting outside the circumferential periphery of the hollow channel, interconnects radially outside the hollow channel, the portions being slidable in the slots.

4. The apparatus of claim 2, wherein the portion of the mover external to the hollow channel comprises a ring, and wherein the portions slidable in the slots comprise respective limbs extending inwardly from the ring.

5. The apparatus of claim 1, wherein the mover is configured to apply to the stent-valve a longitudinal driving force from radially outside the hollow channel.

6. The apparatus of claim 5, further comprising a driver mountable radially outside the hollow channel, and operable to generate the longitudinal driving force relative to the hollow channel and apply the longitudinal driving force from radially outside the channel, through the mover, to a stent-valve within the hollow channel.

7. The apparatus of claim 1, further comprising a driver coupled by a screw thread to the exterior of the hollow channel, for generating the longitudinal driving force in response to rotation of the driver.

8. The apparatus of claim 1, wherein the hollow channel has an entrance and an exit, the entrance having a larger bore diameter than the exit, and the apparatus further comprising a loading tube usable at, or insertable at least partly into, the exit, the loading tube having a bore for receiving at least one of (i) at least a portion of a sheath of a delivery catheter to be loaded with the stent-valve; or (ii) at least a portion of the stent-valve.

9. The apparatus of claim 1, wherein the hollow channel has an entrance and an exit, the entrance having a larger bore diameter than the exit, and the apparatus further comprising a loading tube removably attachable to the hollow channel, the loading tube having a bore therein about equal in diameter to the bore diameter at the exit of the hollow channel to define an extension thereof.

10. The apparatus of claim 1, wherein the portion of the mover fitting outside the circumferential periphery of the hollow channel is dimensioned such that said portion remains outside the circumferential periphery at least along the entire length of the slot.

11. The apparatus of claim 10, wherein the portion of the mover fitting outside the circumferential periphery of the hollow channel has a dimension in a circumferential direction that is greater than a circumferential width of the slot.

12. An apparatus for compressing a transcatheter cardiac stent-valve, the apparatus comprising:
   a hollow channel having an interior surface shaped for progressively compressing the stent-valve in response to longitudinal advancement of the stent within the hollow channel, the hollow channel comprising at least one slot through a wall thereof;
   a mover comprising a portion fitting outside the circumferential periphery of the hollow channel and a portion slidable in the slot and projecting therethrough for engaging the stent-valve within the hollow channel, for applying to the stent-valve a longitudinal driving force from outside the hollow channel; and
   a driver coupled by a screw thread to the exterior of the hollow channel, for generating the longitudinal driving force in response to rotation of the driver.

13. The apparatus of claim 12, wherein the hollow channel comprises a plurality of said slots, and wherein the mover comprises a corresponding number of portions slidable in the slots and projecting therethrough for engaging the stent-valve within the channel.

14. The apparatus of claim 13, wherein the portion of the mover fitting outside the circumferential periphery of the hollow channel, interconnects radially outside the hollow channel, the portions being slidable in the slots.

15. The apparatus of claim 13, wherein the portion of the mover external to the hollow channel comprises a ring, and wherein the portions slidable in the slots comprise respective limbs extending inwardly from the ring.

16. The apparatus of claim 12, wherein the portion of the mover slidable in the slot is shaped as a blade having a thin leading edge or surface that advances within the slot, and a long edge or surface that slides against the edge of the slot.

17. The apparatus of claim 12, wherein the hollow channel has an entrance and an exit, the entrance having a larger bore diameter than the exit, and the apparatus further comprising a loading tube usable at, or insertable at least partly into, the exit, the loading tube having a bore for receiving at least one of (i) at least a portion of a sheath of a delivery catheter to be loaded with the stent-valve; or (ii) at least a portion of the stent-valve.

18. The apparatus of claim 12, wherein the hollow channel has an entrance and an exit, the entrance having a larger bore diameter than the exit, and the apparatus further comprising a loading tube removably attachable to the hollow channel, the loading tube having a bore therein about equal in diameter to the bore diameter at the exit of the hollow channel to define an extension thereof.

19. The apparatus of claim 12, wherein the portion of the mover fitting outside the circumferential periphery of the hollow channel is dimensioned such that said portion remains outside the circumferential periphery at least along the entire length of the slot.

20. The apparatus of claim 19, wherein the portion of the mover fitting outside the circumferential periphery of the hollow channel has a dimension in a circumferential direction that is greater than a circumferential width of the slot.

* * * * *